United States Patent [19]

Hiroki et al.

[11] Patent Number: 5,980,879
[45] Date of Patent: *Nov. 9, 1999

[54] DEODORANT RESIN COMPOSITION AND PROCESS FOR PRODUCTION THEREOF

[75] Inventors: Ishikawa Hiroki, Kanonji; Norihiko Ishikawa, Kawanoe; Naoki Ohba, Kakegawa; Shingo Mukaida, Kyoto; Takeru Mori, Kyoto; Kenji Tanaka, Kyoto, all of Japan

[73] Assignee: Uni-Charm Corporation, Ehima, Japan

[ * ] Notice: This patent issued on a continued prosecution application filed under 37 CFR 1.53(d), and is subject to the twenty year patent term provisions of 35 U.S.C. 154(a)(2).

[21] Appl. No.: 08/860,225

[22] PCT Filed: Dec. 21, 1995

[86] PCT No.: PCT/JP95/02620

§ 371 Date: Aug. 19, 1997

§ 102(e) Date: Aug. 19, 1997

[87] PCT Pub. No.: WO96/19539

PCT Pub. Date: Jun. 27, 1996

[30] Foreign Application Priority Data

Dec. 22, 1994 [JP] Japan ................................. 6-336000

[51] Int. Cl.$^6$ .......................................... A61L 11/00
[52] U.S. Cl. ..................... 424/76.1; 424/76.5; 424/76.6
[58] Field of Search .................................. 424/76.1, 76.5, 424/76.6

[56] References Cited

FOREIGN PATENT DOCUMENTS

| 59-179114 | 10/1984 | Japan | B01D 21/01 |
| 59-189854 | 10/1984 | Japan | A61L 9/01 |
| 1-164436 | 6/1989 | Japan | B01J 20/26 |
| 4-120176 | 4/1992 | Japan | C08L 101/08 |

OTHER PUBLICATIONS

Ryan et al, Chemical Abstracts, vol. 115, #214963, Aug. 22, 1992.

*Primary Examiner*—Jose' G. Dees
*Assistant Examiner*—Kathryne E. Shelborne
*Attorney, Agent, or Firm*—Pollock, Vande Sande & Amernick

[57] ABSTRACT

A particulate deodorant resin composition comprising a water-absorbent resin and powdery zeolite dispersed within the resin particles. The composition exhibits the effect of deodorizing the absorbed body fluid while retaining the water-absorbent function inherent in water-absorbent resins. When, therefore, used as sanitary materials such as paper diaper or sanitary goods, it is featured by not only the inherent absorbent effect, but also the deodorant effect.

10 Claims, No Drawings

DEODORANT RESIN COMPOSITION AND PROCESS FOR PRODUCTION THEREOF

TECHNICAL FIELD

The present invention relates to a resin composition excellent in absorbing property and deodorant property and particularly suited for use in absorbent articles for absorbing urine, blood, body fluids, menstrual blood and so forth, and to a method of producing the same.

BACKGROUND ART

Water absorbent resins are used owing to their absorbing property, water retaining property and gelling ability, in various fields, for example in absorbent articles such as paper diapers, incontinence pads, sanitary napkins and breast milk pads, and in drip absorbents, freshness preservatives, sheets for pets, excretion treatment agents, waste blood gelling agents, etc. However, while absorbent resins are excellent in the ability to absorb and retain urine, blood, body fluids, menstrual blood and the like, they can hardly show deodorant function. Therefore, since such liquids as urine, blood and body fluids have unpleasant characteristic odors and, further, are apt to readily rot under the influence of air and/or bacteria to give off offensive odors due to decay, the advent of a material capable of producing both absorbent and deodorant effects has been awaited from a hygienic viewpoint.

As means of satisfying both these requirements, the following have been proposed, among others: a mixture of an absorbent resin in powder form and zeolite in powder form (Japanese Kokai Publication Sho-57-25813, Sho-59-179114 and Sho-59-189854), a composition comprising active carbon coated with an absorbent resin (Japanese Kokoku Publication Sho-56-31425), a composition comprising an absorbent resin and an antimicrobial agent (Japanese Kokai Publication Hei-03-14867) and like compositions to be applied in absorbent articles; and an absorbent material prepared by admixing a zeolite slurry with a polymerization solution prior to polymerization and, after effecting polymerization, spraying the reaction mixture to a nonwoven fabric, followed by drying (Japanese Kokai Publication Hei-02-84957).

However, when these compositions are applied to absorbent articles, the deodorant effect obtained is not always satisfactory. That is to say, in the case of the mixture of an absorbent resin and zeolite, body fluids such as urine, blood, body fluid, menstrual blood is mostly absorbed and retained by the absorbent resin, since zeolite has little absorbent function. Therefore, in spite of the fact that the body fluid occurring within the absorbent resin is an odor source, the deodorant component zeolite exists apart from the odor source. This is presumably the reason why the deodorant effect cannot be produced to a satisfactory extent. Furthermore, the mixture of an absorbent resin and zeolite powder, when given vibrations or shock, may possibly separate into both components or, when applied to absorbent articles, may possibly allow localization of the absorbent resin and, therefore, of zeolite, with the result that the deodorant effect can be produced only to an unsatisfactory extent. For the production of a much better deodorant effect, it is desirable that the deodorant component should be disposed in contact with the body fluid odor source.

As for the composition comprising active carbon coated with an absorbent resin, active carbon itself is scanty in deodorant effect and, in addition, there is a problem that only limited kinds of odors can be adsorbed.

As regards the composition comprising an absorbent resin and an antimicrobial agent, those containing certain kinds of antimicrobial agents are effective to a certain extent in preventing bacteria and the like from causing decay but are scarcely effective against the characteristic odors intrinsic to body fluids itself. In addition, it is a draw back of such composition that no effect can be observed at all against those odors which result from the oxidative action of air.

Finally, a problem of the absorbent material prepared by admixing a zeolite slurry with a polymerization solution prior to polymerization and, after effecting polymerization, spraying the reaction mixture to a nonwoven fabric, followed by drying is that since the polymerization is carried out after dispersing zeolite in the polymerization solution, low-molecular-weight polymerizable monomers are adsorbed on pore inside surfaces of zeolite particles and thereafter polymerized to block up the pores and thus decrease the deodorant effect.

SUMMARY OF THE INVENTION

In view of the foregoing, the present inventors made intensive investigations in an attempt to develop a deodorant resin composition excellent in both absorbent performance and deodorant performance, in particular suited for use in absorbent articles intended to absorb urine, blood, body fluids, menstrual blood, etc. and a method of producing the same and, as a result, they have now completed the present invention.

Thus, the present invention consists in a deodorant resin composition in powder or granular form which comprises particles of a water absorbent resin (A) and a zeolite powder (B) dispersed within said particles, and a method for producing a deodorant resin composition in powder or granular form comprising particles of a water absorbent resin (A) and a zeolite powder (B) dispersed within said particles, which method comprises kneading together said resin (A) and said zeolite powder (B) in the presence of water, followed by drying and grinding.

While the zeolite powder (B) is dispersed within particles of the absorbent resin (A), the production method involves grinding of the dried resin composition, so that the zeolite partly occurs fixedly on the particle interface or particle surface as well.

DETAILED DESCRIPTION OF THE INVENTION

The water absorbent resin (A) to be used in the practice of the present invention may be any of those water absorbent resins which contain, as constituent units thereof, hydrophilic groups such as carboxylic acid (salt) groups [i.e. carboxylic acid groups and/or its salt groups; hereinafter the same shall apply], sulfonic acid (salt) groups, tertiary amino groups, quaternary ammonium salt groups, hydroxyl groups, amide groups, polyethylene oxide groups and the like. The resin species and production method are not critical. Examples of resin (A) which are suited for use in the practice of the present invention are such crosslinked starch-acrylic acid (salt) copolymers as those described in Japanese Kokoku Publications Sho-53-46199 and Sho-53-46200 and elsewhere, such crosslinked or self-crosslinked polyacrylic acid salts prepared by reversed phase suspension polymerization as those described in Japanese Kokoku Publication Sho-54-30710, Japanese Kokai Publication Sho-56-26909 and elsewhere, such crosslinked polyacrylic acids (salts) prepared by aqueous solution polymerization (adiabatic polymerization, thin film polymerization, spray polymerization, etc.) as those described in Japanese Kokai Publication Sho-55-133413 and elsewhere, such saponified copolymers of a vinyl ester and an unsaturated carboxylic acid or a derivative thereof as those described in Japanese Kokai Publication Sho-52-14689 and Sho-52-27455 and elsewhere, such sulfonic acid (salt) group-containing water absorbent resins as those described in Japanese Kokai Publication Sho-58-2312 and Sho-61-36309 and elsewhere, crosslinked isobutylene-maleic anhydride copolymers, hydrolyzed starch-acrylonitrile copolymers, crosslinked carboxymethylcellulose derivatives, crosslinked polyethylene oxide derivatives, crosslinked polyvinyl alcohol derivatives, partially hydrolyzed polyacrylamides and the like. Two or more of such water absorbent resins may be used combinedly. Water absorbent resins derived from such water absorbent resins by further surface crosslinking are also suited for use in the practice of the present invention.

Preferred water absorbent resins are waster-insoluble ones whose main constituent units are acrylic acid and an acrylic acid salt because such resins show relatively high absorbency.

In the case of water-insoluble water absorbent resins whose main constituent units are acrylic acid and an acrylic acid salt, the mole ratio between the acrylic acid component and acrylic acid salt component is preferably in the range of 50:50 to 10:90, more preferably 40:60 to 25:75. When acrylic acid units remain in the absorbent resin in that manner, the carboxyl groups of such acrylic acid units exhibit the effect of adsorbing ammonia or the like which is one of odor constituents. In cases where the mole ratio of acrylic acid units relative to the sum of the acrylic acid component plus acrylic acid salt component exceeds 50%, the absorbent performance becomes poor and, in addition, the deodorant resin composition obtained has an acidic pH, which is unfavorable from the dermal safety hazard viewpoint. When said mole ratio of acrylic acid units is below 10%, the deodorant resin composition obtained has an alkaline pH and, in this case, too, dermal safety hazard is a matter of concern.

The water absorbent resin (A) mentioned above generally has an absorbency under normal pressure of not less than 30 g/g, preferably 35 to 80 g/g, more preferably 40 to 75 g/g, for physiological saline solution (0.9% aqueous solution of sodium chloride). The absorbency under load of said resin for physiological saline solution is generally not less than 10 g/g, preferably 15 to 60 g/g, more preferably 20 to 50 g/g. The absorbency under normal pressure and absorbency under load are measured by the methods mentioned later herein.

The resin (A) and the deodorant resin composition have a powder or granular form without any particular limitation imposed thereon. Thus, they may have a granular, agglomerated, granulated, lamellar, lump-like, pearl-like or fine powder form, for instance. Preferred are powder or granular forms with a particle size distribution such that not less than 90% by weight of the particles have a size less than 1 mm. Particularly preferred are granular, agglomerated, granulated, lamellar and lump-like forms having a particle size distribution such that not less than 90% by weight of the particles have a size of 0.1 to 0.9 mm.

In the practice of the present invention, the zeolite powder (B) may be either a natural species or a synthetic one. Those synthetic zeolites which are commercially available and stably obtainable are preferred, however. Generally, zeolites are alumino silicates having a three-dimensional skeletal structure and may be represented by the general formula $aM_{2/n}O \cdot xAl_2O_3 \cdot ySiO_2 \cdot zH_2O$, wherein a, x, y and z respectively represents the numbers of units or molecules of a metal oxide, aluminum oxide, silicon oxide and water of crystallization and each is an integer, and M is a cation. As said cation, there may be mentioned alkali metal ions (sodium ion, potassium ion), alkaline earth metal ions (calcium ion, magnesium ion), ammonium ion, etc. Preferred cations are alkali metal ions, and the sodium ion is particularly preferred. The number n is the valence of the cation. The proportions of x:y are not critical but are generally within the range of 1:1 to 1:10, preferably about 1:2 to 1:5. Although water of crystallization is included in synthetic zeolites for reasons concerned with the synthetic process, the number z has no critical importance.

Examples of such zeolites include, but are not limited to, zeolite A, zeolite X, zeolite Y, zeolite T, zeolite containing high level of silica, and the like. Among these, zeolite A, zeolite X and zeolite Y are preferred because of their high deodorant effect; and zeolite A is most preferred.

The particle size of (B) is not critical. From the viewpoint that a more stable deodorant effect should be obtained, however, relatively small particle sizes are preferred. Generally, the mean particle size of (B) is 0.1 to 10 $\mu$m, preferably 0.5 to 5 $\mu$m, more preferably 1 to 4 $\mu$m. When the mean particle size is smaller than 0.1 $\mu$m, dusting and other powder handling-related problems tend to arise, although the deodorant effect may increase. When the mean particle size is over 10 $\mu$m, the surface area becomes small, so that the deodorant effect will be decreased. The term "mean particle size" as used herein is that of primary particles. Granules with a size larger than 10 $\mu$m as prepared from such primary particles by an appropriate granulation procedure are also suited for use in the practice of the present invention.

As regards the pore size of (B), a smaller size is preferred from the viewpoint that a better deodorant effect could be produced. The pore size is generally 1 to 9 angstroms, preferably 3 to 5 angstroms. Pore sizes exceeding 9 angstroms lead to a decreased deodorant effect since the surface area of (B) becomes small. When the pore size is smaller than 1 angstrom, the ability to adsorb odor-emitting substances having a molecule size larger than the pore size is insufficient, hence the range of application with respect to deodorization is restricted.

In the practice of the present invention, the proportions of (A) and (B) may be varied depending on the desired balance between the absorbent performance and deodorant performance. Generally, the proportions of (A):(B) on the weight basis are 90:10 to 50:50, preferably 80:20 to 60:40, more preferably 75:25 to 65:35. When the proportion of (B) relative to the sum total of (A) plus (B) is below 10% by weight, the composition obtained will have a poor deodorant effect. Conversely, when the proportion of (B) relative to the sum total of (A) plus (B) is 50%, the deodorant effect is already enough. Even when the proportion of (B) is further increased, the deodorant effect will not increase any longer but the absorbent effect will only decrease and, therefore, for securing a certain absorbent performance by application of such composition in absorbent articles, it is necessary to use the composition in large amounts, which is uneconomical. Another problem is that dropping of (B) out of the composition occurs.

As the method of producing the deodorant resin composition comprising (A) and (B) dispersed within particles of (A), there may be mentioned, for example, (1) the method comprising mixing up, by kneading, (B) with a hydrous gel of (A) obtained by allowing (A) to absorb water, followed by drying and grinding, (2) the method comprising mixing up, by kneading, (B) with a hydrous gel-like polymer obtained in the process for producing (A), followed by drying and grinding, and (3) the method comprising preliminarily mixing up (A) in powder form with (B) in powder form, further adding water and kneading the mixture, followed by drying and grinding. The method comprising dispersing (B) in a liquid polymerization mixture in the process of producing (A) and then effecting polymerization, followed by drying and grinding also can give a composition with (B) dispersed within particles of (A), but this method is unfavorable since the problem arises that polymerizable low-molecular-weight monomers are adsorbed on pore inside surfaces of (B) and, upon polymerization, block up zeolite pores, impairing the deodorant effect intrinsic to zeolite.

In the step of adding (B) to a hydrous gel of (A) in the above method (1) or (2), (B) in powder form may be added to the hydrous gel, followed by kneading, or an aqueous dispersion of (B) may be prepared in advance and then added to the hydrous gel of (A), followed by kneading, for instance. Either method may suitably be employed without any particular limitation.

No particular limitation is imposed on the apparatus for kneading (A) with (B) in the presence of water. Thus known conventional apparatuses can be used, for example kneaders, universal mixers, single- or twin-axial kneader-extruders, and meat choppers.

The apparatus for drying the kneaded mixture of the hydrous gel of (A) and (B) is not limited to any particular species, either, but known conventional apparatuses may be used. Mention may be made of, for instance, hot air driers, fluidized bed driers, belt driers, drum driers, Nauta driers, paddle driers, rotary kiln driers and infrared driers. The moisture content after drying is of no critical importance but generally is not higher than 7%.

As the apparatus for grinding the dried material obtained after drying of the kneaded mixture of the hydrous gel of (A) and (B), any known conventional apparatuses can be used, for example hammer mills, pin mills, roll mills, pulverizers, feather mills and cutter mills. After grinding, particle size adjustment may be carried out if necessary. The method of particle size adjustment is not critical. For example, the particle size can be adjusted by sieving, agglomeration, or air classification.

The shape and particle size distribution of the deodorant resin composition of the present invention are of no critical importance. As regards the shape, a granular, agglomerated, granulated, lamellar, lump-like, fine powder or like form may be employed. While no particular limitation is imposed thereon, the particle size distribution is generally such that not less than 90% by weight of particles are within the range of 0.01 mm to 1 mm, preferably 0.1 mm to 0.9 mm.

In the composition of the present invention, there may be incorporated, when necessary or where appropriate, one or more of extenders and additives, such as organic powders (e.g. pulp powder, cellulose derivatives, natural polysaccharides, etc.), inorganic powders (e.g. silica, alumina, bentonite, active carbon, etc.), antioxidants, preservatives, biocides, surfactants, colorants and perfumes. The proportion of these is generally not more than 10% by weight relative to the weight of the deodorant resin composition.

By using the deodorant resin composition of the present invention in various absorbent articles, both the absorbent effect and deodorant effect can be produced each to a satisfactory extent. As regards the method of applying the deodorant resin composition to absorbent articles, mention may be made of, for example, the method comprising scattering the particles between layers, arranged in strata, of a fibrous material, such as pulp or heat-adhesive fiber, the method comprising mixing the particles with a fibrous material, such as pulp or heat-adhesive fiber, and the method comprising sandwiching the particles between two or more sheets of absorbent paper and/or nonwoven fabric.

The level of addition of the resin composition to the absorbent articles may be varied over a wide range according to the species of absorbent article, the size thereof and the desired absorbent performance. When the absorbent article is a paper diaper or an incontinence pad, said level is generally 3 to 20 g/sheet. In the case of sanitary napkins, panty liners, breast milk pads and the like, said level is generally 0.2 to 3 g/piece. In the case of sheet-form articles composed of two or more sheets of absorbent paper or nonwoven fabric sandwiching said composition, about 10 to 80 g/m$^2$ is a suitable addition level.

BEST MODES FOR CARRYING OUT THE INVENTION

The following working examples and comparative examples further illustrate the present invention but are by no means limitative of the scope of the present invention. The absorbency under normal pressure, the absorbency under load, the deodorant effect of each resin composition as such and the deodorant effect of each absorbent article containing such resin composition were determined by the methods mentioned below. Hereinafter, unless otherwise specified, "%" means "% by weight".

(1) Absorbency under normal pressure: One gram of the sample is placed in a tea bag made of a 250-mesh nylon net. The bag is immersed in an excessive amount of physiological saline solution (0.9% aqueous solution of sodium chloride) for 1 hour to allow saline solution absorption, then drawn up and, after 15 minutes of draining, weighed to assess the weight increase.

(2) Absorbency under load: In an acrylic resin cylinder (inside diameter 30 mm, height 60 mm) with a 250-mesh nylon net attached to the bottom, there is placed and uniformly spread 0.1 g of the sample and a load of 20 g/cm$^2$ is applied thereto by placing thereon a weight with an outside diameter of 30 mm. The cylinder is immersed in a petri-dish (diameter: 9 cm) containing 25 ml of physiological saline solution, with the nylon net side on the bottom, for 60 minutes. The value 10 times the weight increase after 60 minutes of immersion is reported as the absorbency under load.

(3) Deodorization test of resin compositions: The sample (0.5 g) and 10 ml of fresh human adult urine are placed in a 30-cc beaker for effecting absorption. This beaker is placed in a 5-liter container, which is then tightly closed. The whole is kept in a constant-temperature chamber maintained at 40° C. for 15 hours. Thereafter, the container is opened in an odor-free room for odor evaluation. The odor intensity is evaluated according to the 6-level criteria mentioned below. The evaluation is performed by 10 panelists who have proved to be capable of judging odors in a T&T olfactometer test. The mean value is reported.

0 No odor.

1 Barely perceptible odor (perception threshold concentration).

2 Slight odor the kind of which is barely recognizable (recognition threshold concentration).

3 Readily perceptible odor.

4 Strong odor.

5 very strong, powerful odor.

(4) Deodorization test of absorbent articles in which the resin compositions are applied:

Preparation of absorbent articles: On a polyethylene sheet cut to a rectangle of 14 cm×35 cm, there is laid a tissue paper sheet of the same size and then, further, a fluff pulp layer having a basis weight of 100 g/cm$^2$. Then, 9.8 g of the sample is scattered uniformly on the fluff pulp layer and, further, a fluff pulp layer having a basis weight of 50 g/cm$^2$, a tissue paper sheet and a nonwoven sheet are laid thereon in that order. This absorbent articles is pressed under a pressure of 5 kg/cm$^2$ for 90 seconds to give a model paper diaper.

Deodorization test of the absorbent articles: Fresh urine (80 ml) was applied to the resin composition-containing absorbent article, the whole is placed in a 5-liter wide-mouthed bottle and the bottle is hermetically closed and kept for 15 hours in a constant-temperature chamber maintained at 40° C. Thereafter, the bottle is opened in an odor-free room for odor evaluation. The odor intensity is evaluated according to the same 6-level criteria as employed in the deodorization test of resin compositions.

(5) Performance testing of absorbent articles:

Absorbency: The absorbent article to be tested is immersed in a large excess of physiological saline solution for 30 minutes, then placed on a wire gauze, drained under a load of 10 kg for 20 minutes, and weighed. The weight increase is reported as the absorbency.

Absorbing speed: Artificial urine (50 ml) is poured, from above, into a cylinder (diameter 30 mm) placed on the test article, and the time required for the liquid to disappear from the top sheet is reported as the absorbing speed.

Rewet quantity: Artificial urine (50 ml) is poured onto the center of the model paper diaper. Ten minutes later, 10 sheets of filter paper (10 cm×10 cm) are piled up on the central part of the paper diaper and placed under a load of 3.5 kg. Three minutes later, the total weight increase of the filter paper sheets is determined and this value is reported as the rewet quantity.

EXAMPLE 1

A one-liter glass reaction vessel was charged with 76.6 g of sodium acrylate, 23 g of acrylic acid, 0.4 g of N,N'-methylenebisacrylamide and 295 g of deionized water, and the vessel contents were maintained at 5° C. with stirring and mixing. Nitrogen gas was blown through the contents to reduce the dissolved oxygen content to 1 ppm or below, and then polymerization was initiated by adding 1 g of a 1% aqueous solution of hydrogen peroxide, 1.2 g of a 0.2% aqueous solution of ascorbic acid and 2.4 g of a 2% aqueous solution of 2,2'-azobisamidinopropane dihydrochloride and conducted the polymerization for about 5 hours to give a hydrous gel-like polymer (I) with an absorbent resin concentration of 25%. A 50% aqueous dispersion (20 parts) of zeolite A ("Toyobuilder", product of Toyo Soda; pore size 4 angstroms, mean particle size 1.5 $\mu$m) was added to 100 parts of said hydrous gel-like polymer while kneading in a kneader, and the mixture was kneaded to give a homogeneous mixture. This mixture was subjected to hot air drying at 130° C. to 150° C., then to grinding on a roll mill, and to particle size adjustment such that particles of 850 $\mu$m to 150 $\mu$m accounted for about 98%, to give a deodorant resin composition. This deodorant resin composition was measured for absorbency under normal pressure, absorbency under load and deodorant effect. The results are shown below in Table 1.

EXAMPLE 2

A one-liter glass reaction vessel was charged with 99.5 g of acrylic acid, 0.5 g of tetraallyloxyethane and 270 g of deionized water and the contents were maintained at 5° C. with stirring. Nitrogen gas was blown through the contents to reduce the dissolved oxygen content to 1 ppm or below and then polymerization was initiated by adding 1 g of a 1% aqueous solution of hydrogen peroxide, 1.2 g of a 0.2% aqueous solution of ascorbic acid and 2.4 g of a 2% aqueous solution of 2,2'-azobisamidinopropane dihydrochloride were added and conducted the polymerization for about 5 hours to give a hydrous gel-like polymer. While kneading this hydrous gel-like polymer on an extruder equipped with a perforated plate, 115 g of a 35% aqueous solution of sodium hydroxide was added, and uniform kneading was effected to give a hydrous gel-like neutralized polymer (II) with an absorbent resin concentration of 25%, with about 73 mole % of acrylic acid units being neutralized. While kneading 100 parts of this gel-like polymer (II) in a kneader, 20 parts of the same 50% aqueous dispersion of zeolite A as used in Example 1 was added and uniform kneading was effected. This mixture was subjected to hot air drying at 130° C. to 150° C., then to grinding on a roll mill, and to particle size adjustment such that particles of 850 $\mu$m to 150 $\mu$m accounted for about 98%, to give a deodorant resin composition. The results of performance characteristics measurement of this deodorant resin composition are shown in Table 1.

EXAMPLE 3

Water (100 parts) was allowed to be absorbed by 10 parts of a commercial absorbent resin ("Sanwet IM-1000", product of Sanyo Chemical Industries; crosslinked starch-sodium acrylate copolymer) to give a hydrous gel-like substance (III). Thereto was added 80 parts of the same 50% aqueous dispersion of zeolite A as used in Example 1, and uniform kneading was effected. While kneading this hydrous gel on a kneader, 20 parts of the same 50% aqueous dispersion of zeolite A as used in Example 1 was added and uniform kneading was effected. This mixture was subjected to hot air drying at 130° C. to 150° C., then to grinding on a roll mill, and to particle size adjustment such that particles of 850 $\mu$m to 150 $\mu$m accounted for about 98%, to give a deodorant resin composition. The results of performance characteristics measurement of this deodorant resin composition are shown in Table 1.

EXAMPLE 4

A deodorant resin composition was obtained in the same manner as in Example 2 except that the 50% aqueous dispersion of zeolite was used in an amount of 10 parts in lieu of 20 parts. The performance characteristics measurement results of this deodorant resin composition are shown in Table 1.

EXAMPLE 5

A deodorant resin composition was obtained in the same manner as in Example 2 except that the 50% aqueous dispersion of zeolite was used in an amount of 30 parts in lieu of 20 parts. The results of performance characteristics measurement of this deodorant resin composition are shown in Table 1.

EXAMPLE 6

A deodorant resin composition was obtained in the same manner as in Example 2 except that the zeolite species used was molecular sieve 3A (Nakalai Tesque reagent grade; pore size 3 angstroms, mean particle size 10 $\mu$m or less). The results of performance characteristics measurement of this deodorant resin composition are shown in Table 1.

EXAMPLE 7

A deodorant resin composition was obtained in the same manner as in Example 2 except that the zeolite species used was molecular sieve 5A (Nakalai Tesque reagent grade; pore size 5 angstroms, mean particle size 10 $\mu$m or less). The results of performance characteristics measurement of this deodorant resin composition are shown in Table 1.

EXAMPLE 8

An absorbent article was produced using the deodorant resin composition of Example 1. The results of performance characteristics measurement of this absorbent article are shown in Table 2.

EXAMPLE 9

An absorbent article was produced using the deodorant resin composition of Example 2. The results of performance characteristics measurement of this absorbent article are shown in Table 2.

EXAMPLE 10

An absorbent article was produced using the deodorant resin composition of Example 3. The results of performance characteristics measurement of this absorbent article are shown in Table 2.

COMPARATIVE EXAMPLE 1

The hydrous gel-like polymer (I) obtained in Example 1 was subjected to hot air drying at 130° C. to 150° C., then to grinding on a roll mill and to particle size adjustment such that particles of 850 $\mu$m to 150 $\mu$m accounted for about 98%, to give a resin powder for comparison. The results of performance characteristics measurement of this powder are shown in Table 1.

COMPARATIVE EXAMPLE 2

The hydrous gel-like neutralized polymer (II) obtained in Example 2 was subjected to hot air drying at 130° C. to 150° C. then to grinding on a roll mill and to particle size adjustment such that particles of 850 $\mu$m to 150 $\mu$m accounted for about 98%, to give a resin powder for comparison. The results of performance characteristics measurement of this powder are shown in Table 1.

COMPARATIVE EXAMPLE 3

The results of performance characteristics measurement of "Sanwet IM-1000" are shown in Table 1 under Comparative Example 3.

COMPARATIVE EXAMPLE 4

A resin composition for comparison was prepared by powder-powder blending of 100 parts of the resin powder obtained in Comparative Example 1 and 40 parts of the same zeolite A species as used in Example 1. The results of performance characteristics measurement of this composition are shown in Table 1.

COMPARATIVE EXAMPLE 5

A resin composition for comparison was prepared by powder-powder blending of 100 parts of the resin powder obtained in Comparative Example 2 and 40 parts of the same zeolite A species as used in Example 1. The results of performance characteristics measurement of this composition are shown in Table 1.

COMPARATIVE EXAMPLE 6

A resin composition for comparison was prepared in the same manner as in Example 2 except that the 50% aqueous dispersion of zeolite was used in an amount of 2 parts in lieu of 20 parts. The performance characteristics measurement results of this composition are shown in Table 1.

COMPARATIVE EXAMPLE 7

A resin composition for comparison was prepared in the same manner as in Example 2 except that the 50% aqueous dispersion of zeolite was used in an amount of 70 parts in lieu of 20 parts. The performance characteristics measurement results of this composition are shown in Table 1.

COMPARATIVE EXAMPLE 8

A resin composition for comparison was prepared in the same manner as in Example 2 except that the zeolite species used was zeolite X with a pore size of 10 angstroms. The results of performance characteristics measurement of this composition are shown in Table 1.

COMPARATIVE EXAMPLE 9

An absorbent article was produced using the resin powder of Comparative Example 1. The results of performance characteristics measurement of this absorbent article for comparison are shown in Table 2.

COMPARATIVE EXAMPLE 10

An absorbent article was produced using the resin powder of Comparative Example 2. The results of performance characteristics measurement of this absorbent article for comparison are shown in Table 2.

COMPARATIVE EXAMPLE 11

An absorbent article was produced using the resin composition of Comparative Example 4. The results of performance characteristics measurement of this absorbent article for comparison are shown in Table 2.

COMPARATIVE EXAMPLE 12

An absorbent article was produced using the resin composition of Comparative Example 5. The results of performance characteristics measurement of this absorbent article for comparison are shown in Table 2.

TABLE 1

|  | Absorbency under normal pressure (g/g) | Absorbency under load (g/g) | Deodorization test |
|---|---|---|---|
| Example |  |  |  |
| 1 | 44 | 24 | 1.8 |
| 2 | 46 | 26 | 1.6 |
| 3 | 50 | 25 | 1.9 |
| 4 | 53 | 22 | 2.8 |
| 5 | 41 | 28 | 1.6 |
| 6 | 47 | 26 | 2.5 |
| 7 | 46 | 25 | 2.4 |
| Comparative Example |  |  |  |
| 1 | 55 | 14 | 4.2 |
| 2 | 58 | 16 | 4.0 |
| 3 | 63 | 9 | 4.1 |
| 4 | 35 | 11 | 2.6 |
| 5 | 38 | 12 | 2.5 |
| 6 | 55 | 15 | 4.2 |
| 7 | 25 | 8 | 1.5 |
| 8 | 45 | 21 | 3.9 |

TABLE 2

|  | Absorbency (g/sheet) | Absorbing speed (sec) | Rewet quantity (g) | Deodorization test |
|---|---|---|---|---|
| Example |  |  |  |  |
| 8 | 408 | 26 | 0.3 | 2.0 |
| 9 | 420 | 25 | 0.2 | 1.9 |
| 10 | 430 | 29 | 0.3 | 2.1 |
| Comparative Example |  |  |  |  |
| 9 | 440 | 29 | 0.2 | 4.4 |
| 10 | 450 | 28 | 0.1 | 4.2 |
| 11 | 320 | 30 | 2.2 | 3.0 |
| 12 | 330 | 27 | 2.0 | 2.9 |

INDUSTRIAL APPLICABILITY

The deodorant resin composition of the present invention has the following features and effects:

(1) It performs not only an absorbent function but also an excellent deodorant function.

(2) Since the deodorant component zeolite is dispersed in the odor source body fluid absorbed by the absorbent resin, the zeolite adsorbs the odor efficiently and exhibits an excellent deodorant effect.

(3) Unlike the powder-powder mixture of (A) and (B), the deodorant resin composition with (B) dispersed within particles of (A) shows an improved absorbency under load.

(4) Unlike the powder-powder mixture of (A) and (B), it will not cause such troubles as separation into both components upon vibrations or shock, or localization of the absorbent resin and zeolite in absorbent articles when said composition is applied thereto.

(5) It can be applied to absorbent articles in the same manner as the conventional absorbent resins.

(6) When applied to absorbent articles, it provides the absorbent articles with a deodorant function and at the same time reduces the rewet quantity. On the contrary, in the case of a powder-powder mixture of (A) and (B), a deodorant function may be provided but the rewet quantity increases.

(7) It can be produced by a simple process which comprises kneading (B) with a hydrous gel of (A), drying and grinding.

The deodorant resin composition of the present invention, which exhibits the effects mentioned above, is particularly suited for use in paper diapers, incontinence pads, sanitary napkins, panty liners, breast milk pads, labor bed (puerperal) mats, underpads for medical use and other various absorbent articles.

Furthermore, it is useful as a gelling agent for various liquids which, upon decay, generate an offensive odor, for example pet urine and waste blood, and it is also useful in the production of sheets for pets, drip absorbents and like sheet or tape form absorbents.

We claim:

1. A deodorant resin composition in powder or granular form which comprises particles of water absorbent rein (A) and a zeolite powder (B) dispersed within said particles;

wherein said deodorant resin composition is produced by the method of (1) kneading a hydrous gel of said resin (A) with said powder (B) in powder form or in aqueous dispersion form followed by drying and grinding the resulting mixture, said hydrous gel being obtained by allowing said resin (A) to absorb sufficient amount of water for gelation; or (2) kneading a hydrous gel-like polymer with said powder (b) in powder form or in aqueous dispersion form, followed by drying and grinding the resulting mixture, said hydrous gel polymer being obtained in the process for producing said resin (A) in an aqueous medium.

2. The composition according to claim 1, wherein the pore size of said (B) is 1 to 9 angstroms, and kneading step in accordance with method (1) and method (2) is conducted in the presence of water with at least 3.2 times the amount of said (A).

3. The composition according to claim 2, wherein the proportion of said (A) to said (B) is 90:10 to 50:50 on the weight basis.

4. The composition according to claim 2, wherein said (A) has a shape of granules having a particle size distribution such that not less than 90% by weight thereof has a size of 0.1 mm to 0.9 mm.

5. The composition according to claim 4, wherein the mean particle size of said (B) is 0.1 to 10 $\mu$m.

6. The composition according to claim 2, wherein said (A) is a water-insoluble water absorbent resin whose main constituent units are acrylic acid and an acrylic acid salt, wherein the mole ration between the acrylic acid component and the acrylic acid salt component is 50:50 to 10:90.

7. An absorbent article which comprises the deodorant resin composition of claim 2.

8. A method for producing a deodorant resin composition in powder or granular form comprising particles of a water absorbent resin (A) and a zeolite powder (B) dispersed within said particles, which method comprises kneading said resin (A) together with said zeolite powder (B) in the presence of water for the gelation of said resin (A), followed by drying and grinding.

9. The method according to claim 8, wherein said (A) is a water-insoluble water absorbent resin whose main constituent units are acrylic acid and an acrylic acid salt.

10. An absorbent article which comprises the deodorant resin composition according to claim 1.

* * * * *

UNITED STATES PATENT AND TRADEMARK OFFICE
CERTIFICATE OF CORRECTION

PATENT NO. : 5,980,879
DATED : Nov. 9, 1999
INVENTOR(S) : Hiroki et al

It is certified that error appears in the above-identified patent and that said Letters Patent is hereby corrected as shown below:

```
Title page, item [73] Assignee: should read
---Uni-Charm Corporation, Ehima, Japan and
Sanyo Chemical Industries, Ltd., Kyoto, Japan--.
```

Signed and Sealed this

First Day of February, 2000

Attest:

Q. TODD DICKINSON

*Attesting Officer*  *Acting Commissioner of Patents and Trademarks*

UNITED STATES PATENT AND TRADEMARK OFFICE
CERTIFICATE OF CORRECTION

PATENT NO. : 5,980,879
DATED : November 9, 1999
INVENTOR(S) : Hiroki et al It is certified that error appears in the above—identified patent and that said Letters Patent is hereby corrected as shown below:

Title page, Item [73] Assignee, should read
---Uni-Charm Corporation, Ehime, Japan and
Sanyo Chemical Industries, Ltd., Kyoto, Japan---.

Signed and Sealed this

First Day of May, 2001

Attest:

NICHOLAS P. GODICI

Attesting Officer

Acting Director of the United States Patent and Trademark Office